United States Patent [19]

Mielke

[11] Patent Number: 5,210,345
[45] Date of Patent: May 11, 1993

[54] PROCESS FOR THE PREPARATION OF VINYL CHLORIDE

[75] Inventor: Ingolf Mielke, Burgkirchen, Fed. Rep. of Germany

[73] Assignee: Hoechst Aktiengesellschaft, Frankfurt am Main, Fed. Rep. of Germany

[21] Appl. No.: 959,040

[22] Filed: Oct. 9, 1992

[30] Foreign Application Priority Data

Aug. 27, 1992 [DE] Fed. Rep. of Germany ....... 4228593

[51] Int. Cl.⁵ ............................................. C07C 17/34

[52] U.S. Cl. .................................... 570/227; 570/226
[58] Field of Search ................................ 570/227, 226

[56] References Cited

U.S. PATENT DOCUMENTS 4,851,597 7/1989 Felix et al. .

Primary Examiner—Howard T. Mars
Attorney, Agent, or Firm—Connolly and Hutz

[57] ABSTRACT

An addition of benzotrichloride produces a significantly higher yield of vinyl chloride in the thermal cleavage of 1,2-dichloroethane.

4 Claims, No Drawings

PROCESS FOR THE PREPARATION OF VINYL CHLORIDE

DESCRIPTION

U.S. Pat. No. 4,851,597 discloses carrying out the thermal cleavage of 1,2-dichloroethane (EDC) to give vinyl chloride (VC) in the presence of trichloroacetyl chloride or a compound having 3 carbon atoms, at least 6 chlorine atoms, 0 or 1 oxygen atom and, per carbon atom bound to this, 0 or 1 hydrogen atom. As a result of these additions, the degree of conversion is increased or, at the same conversion, the cleavage temperature is reduced, as a result of which a reduction of by-products is observed.

Surprisingly, it has now been found that in this reaction, an addition of benzotrichloride effects a still substantially greater increase in conversion. The invention therefore relates to the use of benzotrichloride as an additive in the thermal cleavage of EDC to give VC.

The reaction can be carried out according to the details of U.S. Pat. No. 4 851 597. Preferred embodiments of the invention are described in more detail below:

The thermal cleavage is expediently carried out at 300 to 600° C., at atmospheric pressure or elevated pressure up to about 50 bar (5 MPa). Preference is given to pressures from 10 to 40 bar (1 to 4 MPa).

Even relatively small amounts of benzotrichloride produce significantly increased conversions to VC. Thus, for example, 250 ppm of benzotrichloride increase the VC yield from about 52% (feed EDC without additive) to about 76%. Higher levels of addition cause a further, but not so great, increase in yield.

Surprisingly, moreover, it is shown that the chloral which has to be removed with great effort is formed in a considerably smaller amount.

Benzotrichloride can—as described in U.S. Pat. No. 4,851,597 be added to the prepurified EDC (feed EDC).

The invention is described in more detail in the example below. Percentage figures relate in this to the weight.

EXAMPLE

An apparatus is used comprising a reservoir for EDC, a metering pump, an evaporator tube, packed with glass beads, connected to this and which again is connected to a quartz tube which has an internal diameter of 18 mm and can be heated over a length of 500 mm. The outlet of the quartz tube is connected to three washing flasks, connected in sequence, and a gas collection flask. The first washing flask seen from the end of the quartz tube is furnished with a cooling jacket (water cooling) and serves to condense the unreacted EDC. The second and third washing flasks contain distilled water for trapping the hydrogen chloride resulting from the EDC cleavage. The reaction gases now free of HCl and only containing traces of EDC (VC +by-products) finally pass through a gas collection flask for sampling.

During each experiment, the evaporator tube is heated to 220° C. and the quartz tube to 490° C. (measured at the internal wall of the tube at the end of the heating zone). The reservoir is filled with EDC to which the desired quantity of benzotrichloride has been added. 90 g of EDC per hour run via the metering pump into the heated evaporator tube and are evaporated there. The vapors are passed through the quartz tube (residence time about 10 seconds) and the following washing flasks and the gas collection flask. After steady-state experimental conditions are established, the duration of each experiment is 2 hours. The unreacted dichloroethane condensed out in the first washing flask is then weighed, analyzed for by-products by GC and the hydrogen chloride contained in the EDC is separated off by washing with water. The aqueous phase is combined with the washing waters from the second and third washing flasks and the hydrochloric acid is titrated. This gives the EDC conversion in the quartz tube. The gas sample contained in the gas collection flask is analyzed by GC for VC and by-products.

TABLE

| Addition of benzotrichloride to EDC (feed quality) | | |
|---|---|---|
| Amount (ppm) | Conversion (%) | Chloral content (mg/100 g of EDC) |
| 0 | 51.8 | 0.4 |
| 250 | 75.9 | 0.1 |
| 500 | 81.1 | not detectable |
| 1000 | 85.1 | 0.3 |

The conversion values are averages from at least two determinations.

I claim:

1. A process for preparing vinyl chloride, comprising: thermally cleaving 1,2-dichloroethane in the presence of benzotrichloride.

2. The process as claimed in claim 1, wherein the thermal cleavage is performed at 300° to 600° C. at a pressure from atmospheric pressure to 50 bar.

3. The process as claimed in claim 1, wherein at least 250 ppm of benzotrichloride are added to the 1,2-dichloroethane.

4. The process as claimed in claim 2, wherein at least 250 ppm of benzotrichloride are added to the 1,2-dichloroethane.

* * * * *